(12) United States Patent
Delaney et al.

(10) Patent No.: US 9,039,224 B2
(45) Date of Patent: May 26, 2015

(54) HEAD-MOUNTED POINTING DEVICE

(71) Applicants: Conor P. Delaney, Shaker Heights, OH (US); Nicholas John Gray Swingle, Omaha, NE (US); Kaleigh E. Judson, Chesterland, OH (US); Kristin Bolte, West Chester, OH (US)

(72) Inventors: Conor P. Delaney, Shaker Heights, OH (US); Nicholas John Gray Swingle, Omaha, NE (US); Kaleigh E. Judson, Chesterland, OH (US); Kristin Bolte, West Chester, OH (US)

(73) Assignee: University Hospitals of Cleveland, Cleveland, OH (US)

(*) Notice: Subject to any disclaimer, the term of this patent is extended or adjusted under 35 U.S.C. 154(b) by 0 days.

(21) Appl. No.: 14/037,811

(22) Filed: Sep. 26, 2013

(65) Prior Publication Data
US 2014/0092587 A1 Apr. 3, 2014

Related U.S. Application Data

(60) Provisional application No. 61/706,926, filed on Sep. 28, 2012.

(51) Int. Cl.
| | |
|---|---|
| *F21V 21/084* | (2006.01) |
| *F21V 33/00* | (2006.01) |
| *G02B 27/20* | (2006.01) |
| *A61B 19/00* | (2006.01) |

(52) U.S. Cl.
CPC ........... *F21V 33/0068* (2013.01); *F21V 21/084* (2013.01); *G02B 27/20* (2013.01); *A61B 2019/202* (2013.01); *A61B 2019/262* (2013.01); *A61B 19/5202* (2013.01)

(58) Field of Classification Search
CPC ... F21V 33/0068; F21V 21/084; G02B 27/20; A61B 2019/202; A61B 2019/262; A61B 19/5205
USPC ......... 362/103, 105, 106, 553, 570, 572, 259, 362/457
See application file for complete search history.

(56) References Cited

U.S. PATENT DOCUMENTS

| | | | | |
|---|---|---|---|---|
| 3,890,646 | A * | 6/1975 | Fassett et al. | 2/8.3 |
| 5,481,622 | A * | 1/1996 | Gerhardt et al. | 382/103 |
| 5,774,271 | A * | 6/1998 | Lagerway et al. | 359/649 |
| 6,097,373 | A * | 8/2000 | Jakobs | 345/168 |
| 6,224,227 | B1 * | 5/2001 | Klootz | 362/105 |
| 6,545,664 | B1 | 4/2003 | Kim | |
| 6,672,972 | B1 * | 1/2004 | Stone | 473/207 |
| 6,801,231 | B1 | 10/2004 | Beltz | |
| 7,207,896 | B1 * | 4/2007 | Sudol | 473/268 |
| 7,722,205 | B2 | 5/2010 | Kim | |
| 2002/0071287 | A1 * | 6/2002 | Haase | 362/553 |
| 2003/0164172 | A1 * | 9/2003 | Chumas et al. | 128/898 |
| 2004/0027691 | A1 | 2/2004 | Himmele | |
| 2005/0162380 | A1 | 7/2005 | Paikattu et al. | |
| 2006/0285315 | A1 * | 12/2006 | Tufenkjian | 362/105 |
| 2009/0024161 | A1 * | 1/2009 | Bonutti et al. | 606/213 |
| 2011/0125021 | A1 | 5/2011 | Sudol | |
| 2012/0229248 | A1 * | 9/2012 | Parshionikar et al. | 340/3.1 |
| 2012/0235909 | A1 * | 9/2012 | Birkenbach et al. | 345/158 |
| 2013/0090931 | A1 * | 4/2013 | Ghovanloo et al. | 704/275 |

* cited by examiner

*Primary Examiner* — Anh Mai
*Assistant Examiner* — Glenn Zimmerman
(74) *Attorney, Agent, or Firm* — Richard M. Klein; Fay Sharpe LLP

(57) ABSTRACT

A head-mounted pointing device is disclosed, and can be used for example for surgical training. The pointing device includes a frame or harness assembly made from a circumferential headband and a cross strap that extends over the user's (i.e. trainer's) head. A laser pointer is mounted on one side of the circumferential headband, and a battery pack is provided to power the laser pointer. An user-operated pneumatically controlled switch is used to toggle the laser pointer. By moving the user's head and by activating the switch to engage the laser pointer, the trainer can point to a given target, such as material to be surgically excised from the patient during a surgical procedure.

14 Claims, 6 Drawing Sheets

HEAD-MOUNTED POINTING DEVICE

CROSS-REFERENCE TO RELATED APPLICATIONS

This application claims priority to U.S. Provisional Patent Application Ser. No. 61/706,926, filed on Sep. 28, 2012. The entirety of that disclosure is hereby fully incorporated by reference.

BACKGROUND

The present disclosure relates to a pointing device worn on the head of a user. It finds particular application in conjunction with training for surgical education, and will be described with particular reference thereto, although it can be used for many other purposes such as teaching of combined skills where hands-free pointing, spotting, indicating, or directing is useful.

Part of the training process to become a board eligible surgeon involves completion of a residency program. In the residency program, the resident doctor will perform surgical procedures on a consenting patient under the supervision of a trainer surgeon.

When taking a surgical resident through a procedure, the trainer's hands are often busy performing the steps of the operation, and instructions and directions must be given verbally. This is true for both laparoscopic and open procedures. In addition, the surgical resident is usually participating in the procedure as well, wielding surgical instruments such as a scalpel or other cutting or suturing implements. It would be helpful for the trainer to have a pointing device that can be worn and used to accurately direct the trainee where to focus and dissect, suture, cauterize, etc., in the patient.

BRIEF DESCRIPTION

The present disclosure relates to a pointing device that can be worn on a user's head, such as the head of a trainer teaching surgical procedures. The pointing device includes a laser pointer that provides a dot or beam of light at a location dictated by the user, such as to certain tissue to be excised from a patient. An user-operated pneumatically controlled switch is provided so that the dot/beam can be toggled on or off by the user without manual intervention. The switch can be controlled by the users breath. The pointing device also includes a band/strap assembly for forming a head harness for mounting the laser pointer and switching mechanism to the head of the user. By moving the user's head and by activating the switch to engage the laser pointer, the user can point to a given target, such as tissue to be excised from a patient, during a surgical procedure.

Disclosed in embodiments herein is an adjustable head-mounted pointing device that comprises a circumferential headband; a cross strap extending between opposite sides of the circumferential headband; a laser pointer mounted on one side of the circumferential headband; a battery pack; and a pneumatically controlled switch for activating the laser pointer. The laser pointer is an electronic device that converts input power into a narrow beam of coherent light that is used to disclose a targeted area by the user upon activation.

The battery pack can be mounted at the center of the cross strap. Alternatively, the battery pack can be mounted on the side of the circumferential headband opposite the laser pointer. In other embodiments, the battery pack can be mounted on the side of the circumferential headband behind the laser pointer.

The laser pointer may emit a red or green colored light beam. Other color or color combinations are also contemplated, as well as dual colors or multiple color combination lasers. For example, the color green may be used by the trainer to indicate to proceed forward, red to halt, etc.

An adjustment device or dial may be present on a rear side of the circumferential headband for controlling the circumference of the headband.

The pointing device may sometimes further comprise a mount on a front side of the circumferential headband, the mount having an arm and a grip. Other times, the pointing device further comprises at least one longitudinally-oriented catch on the cross strap. The pointing device could further comprise at least one vertically-oriented catch on the circumferential headband.

The laser pointer may include a base and a muzzle. The pneumatically controlled switch may include a means for conveying pneumatic pressure, such as a straw connected to a pressure transducer.

Also described in embodiments is a head-mounted pointing device that comprises a frame formed from a circumferential headband and a cross strap that extends between opposite sides of the circumferential headband; a battery pack mounted at the center of the cross strap; a laser pointer mounted on one side of the circumferential headband, the laser pointer having a base and a muzzle; a pneumatically controlled switch for controlling the laser pointer, the switch including a flexible straw extending from the base of the laser pointer; means for changing the size of the circumferential headband; means for changing the size of the cross strap; and a mount on a front side of the circumferential headband, the mount having an arm and a grip.

Methods of using a head-mounted pointing device to point to a given target during a surgical procedure are also disclosed. The head-mounted pointing device is donned by the user, such as the surgical trainer. The laser pointer of the pointing device is engaged or toggled on by breathing (e.g. puffing) at a pneumatically controlled switch to activate a laser beam. The laser beam is then pointed at the given target.

The laser pointer of the pointing device can be disengaged or the toggled off by breathing (e.g. sipping or sucking) at the pneumatically controlled switch to deactivate the laser beam.

The pneumatically controlled switch sometimes uses a binary control. Other times, the pneumatically controlled switch uses sip-and-puff control.

The method may use any of the various embodiments of a head-mounted pointing device described herein.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

A more complete understanding of the compositions and methods disclosed herein can be obtained by reference to the accompanying drawings. These figures are merely schematic representations based on convenience and the ease of demonstrating the present disclosure, and are, therefore, not intended to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The present disclosure relates to a pointing or spotting device that can be worn on the head of the user. As previously noted, such a pointing device can be useful for a trainer surgeon/trainer of surgical procedures who is working with a surgical resident or trainee. Teaching in the operating room is particularly difficult in laparoscopic cases, because it is difficult to demonstrate on the laparoscopic instrument screen where the trainee should direct their attention or where they should operate, when the trainer's hands are busy. The pointing device can be used to visually indicate a particular location to the surgical resident instead of through spoken words.

However, the pointing device cannot simply be an always-on device. For example, the trainer may wish to indicate a location where the surgical resident should dissect (i.e. cut). However, with an always-on device, the surgical resident may continue dissecting at the indicated location when the trainer wishes dissection to stop. A switch is required to deactivate the pointing device. However, the hands of the trainer surgeon are sterile, and the feet of the trainer surgeon may be operating other instruments. Thus, a different switching mechanism must be used.

Figure 1:
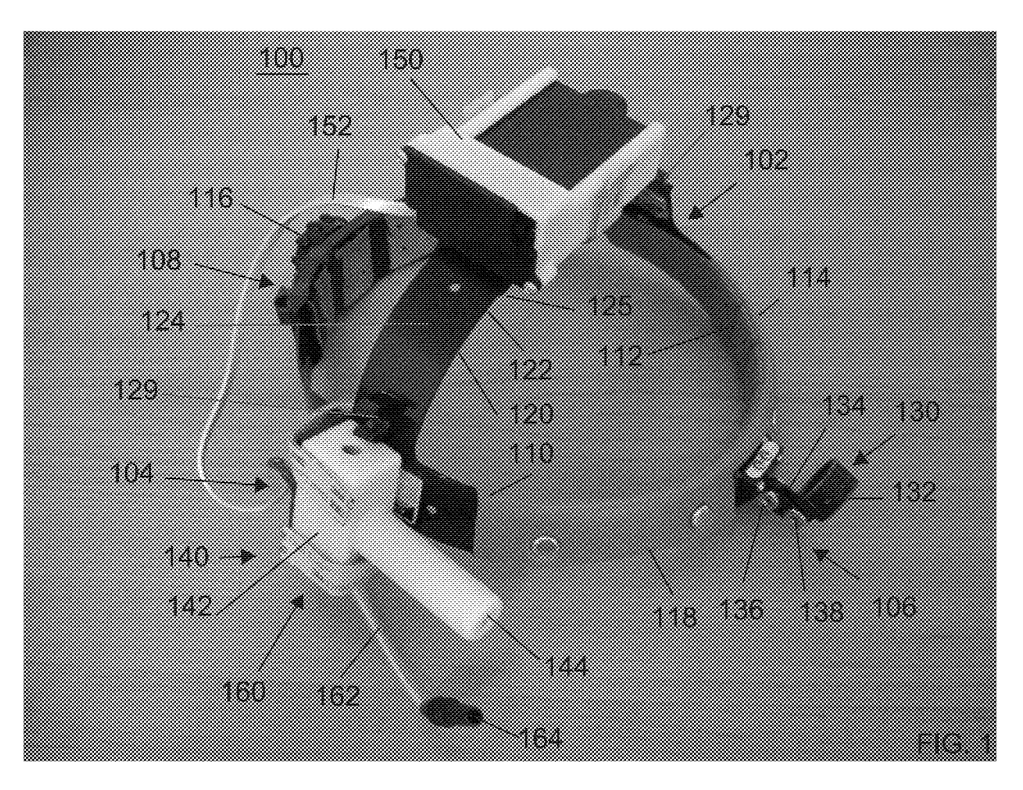
FIG. 1 is a side perspective view of a prototype of the head-mounted pointing device of the present disclosure.
Figure 2:
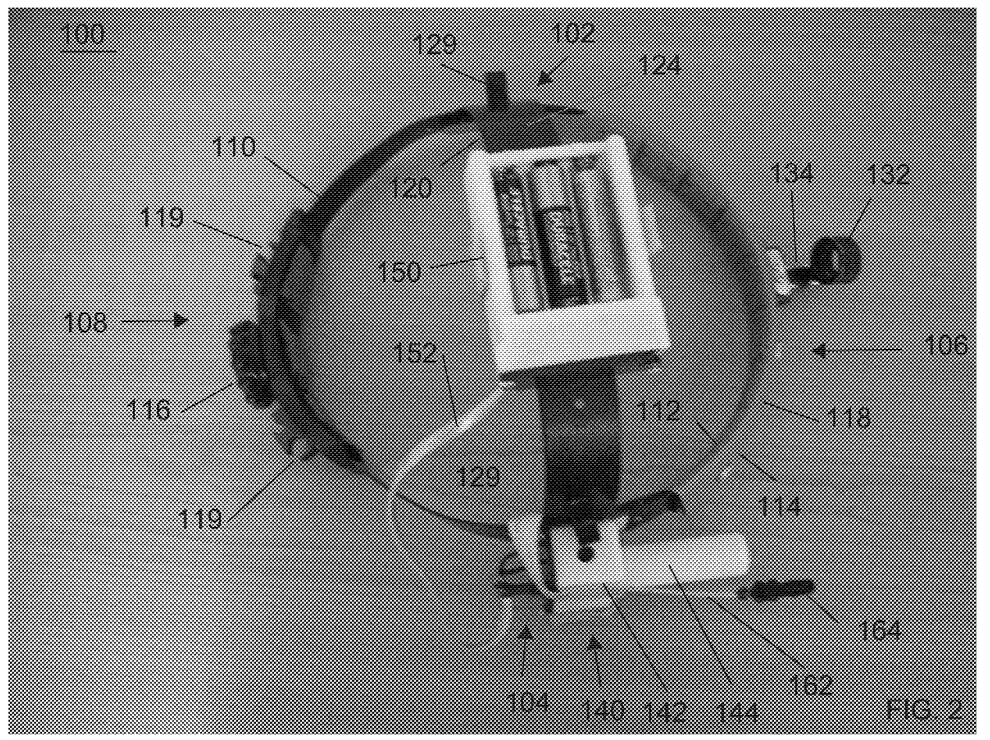
FIG. 2 is a top view of the prototype of FIG. 1.
Figure 3:
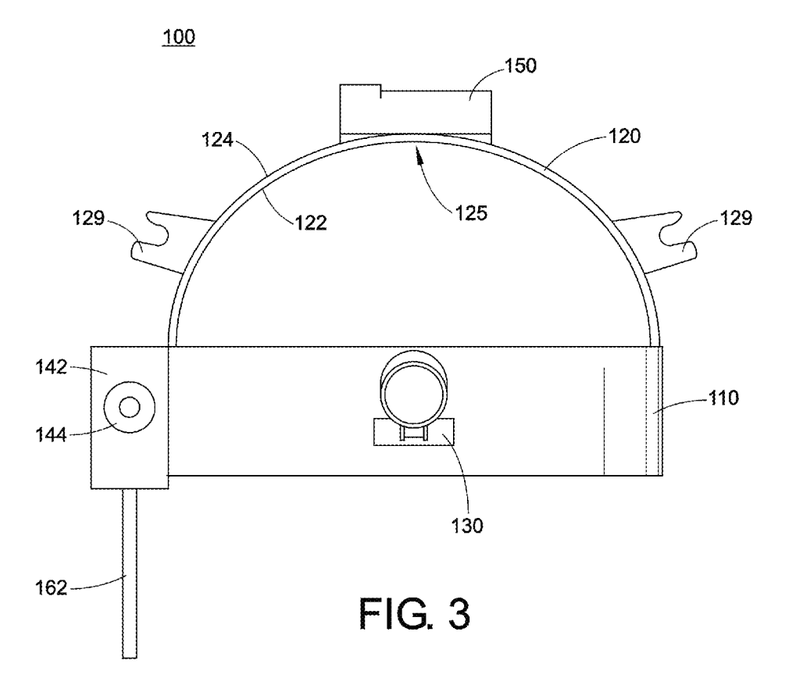
FIG. 3 is a front view of the prototype of FIG. 1.

FIG. 1 is a right side perspective view of a prototype of the head-mounted pointing device of the present disclosure. FIG. 2 is a top view of the prototype device. FIG. 3 is a front view of the prototype device. This device may also be considered to be a laser headlight, or a hands-free device, or a head-mounted laser pointer, or headgear with a mounted pointing device.

The head-mounted pointing device 100 includes a frame formed from a circumferential headband 110 and a cross strap 120. The circumferential headband extends around the wearer's head, and has an interior surface 112 and an exterior surface 114 (see FIG. 2 for a better view of these two surfaces). The cross strap 120 extends between opposite sides (usually the left side 102 and the right side 104) of the circumferential headband, and passes over the wearer's head. It is contemplated that the cross strap passes between the ears of the user, for comfort. The cross strap 120 also has an interior surface 122 and an exterior surface 124 (see FIG. 3 for a better view of these two surfaces). The cross strap may be described as a half circle, and the circumferential headband may be described as a full circle. The frame can be made in several different ways. The size of the circumferential headband can be adjusted; for example, as illustrated here, a dial 116 is present on the rear side 108 of the circumferential headband to control its circumference. Similarly, the size of the cross strap can also be adjusted. These allow the frame to be fitted to the head of the user and worn comfortably. The frame can be made of any suitable material. For example, the frame can be made of plastic, cloth, etc. here, a padding 118 is present on the front side 106 of the circumferential headband. The circumferential headband on the cross strap may be made as one integral piece, or may be made as separate components that are later joined together.

It is contemplated that additional attachment means may be present on the frame for holding other tools or equipment. For example, also visible on the front side 106 of the frame is a mount 130 that extends outwardly from the exterior surface 114 of the circumferential headband. The mount includes an arm 134 and a grip 132 at the end of the arm. The arm is adjustable at both ends 136, 138 for positioning the grip as desired. It is contemplated that, for example an illumination light can be held by the grip to provide illumination to the user. This light (not shown) is usually oriented in a different direction from that of the laser pointer. As another example, a longitudinally-oriented molded catch 129 is also present on either side of the cross strap 120, and can be used to hold additional items as desired by the user. As yet another example, also visible in FIG. 2 are two vertically oriented molded catches 119 located on the rear side 108 of the circumferential headband. However, it should be clear that embodiments are contemplated in which these additional attachment means are not present.

A laser pointer 140 is mounted to one side of the circumferential headband. As illustrated here, the laser pointer is mounted on the right side 104 of the frame, where the cross strap 120 connects to the headband 110. The laser pointer 140 is mounted to one side of the circumferential headband, i.e. on the left side 102 or right side 104 of the user's head, rather than directly in front (i.e. on the user's forehead). The laser pointer typically emits a red or green color, which provides for visual distinction against the background. The power of the laser pointer is very low, usually 5 miiliwatts (mW) or less. The laser pointer can be mounted to the circumferential headband using generally known means such as hook-and-loop fasteners, adhesive, etc. As illustrated here, the laser pointer 140 includes a base 142 and a muzzle 144. The muzzle points in the direction in which the laser light will be emitted, towards the front of the frame.

A battery pack 150 is included to provide power to the laser pointer. A wire 152 connects the battery pack 150 to the laser pointer 140. As illustrated here, the battery pack is placed at the center 125 of the cross strap, i.e. on top of the user's head, for balance. However, it is possible for the battery pack to be mounted anywhere on the headband 110 or the cross strap 120. For example, the battery pack could be mounted on the side of the circumferential headband opposite the laser pointer. Alternatively, the battery pack could be attached to the circumferential headband behind the laser pointer 140. Desirably, the battery pack is placed to minimize neck strain. The battery pack contains standard batteries, e.g. AA, AAA. C, D, 9-volt, button/coin cells, etc.

A pneumatically controlled switch 160 is used to turn the laser pointer 141 on or off. The switch includes a pressure transducer (not visible) and a straw 162 which extends from the laser pointer down towards and off to one side of the users mouth. The straw is detachable (for replacement as needed) and flexible (for customization to the user). A mouthpiece 164 is located at the free end of the straw. As illustrated here, the pressure transducer is located within the base of the laser pointer, and the straw 162 and mouthpiece 164 are visible.

It is contemplated that the laser pointer can be activated or controlled by blowing into the straw to toggle the laser pointer on and off. This can be done using a binary control, where the on/off state of the laser pointer is stored and switched with each breath registered by the switch. Alternatively, a "sip-and-puff" style of control may be used. For example, a higher-than-normal atmospheric air pressure can be produced by puffing and blowing into the straw, and this higher air pressure could be used to turn on the laser pointer. A lower-than-normal atmospheric air pressure can be produced by sipping or sucking against the straw, and this lower air pressure could be used to turn off the laser pointer. This pneumatically controlled switch may also be referred to as a blow switch. The pneumatically controlled switch operates by detecting a change in pressure exerted by the users breathing.

In other embodiments, it is also contemplated that the laser pointer is able to produce multiple colors, or that two or more laser pointers emitting different colors are placed on the head-mounted pointing device. To control the different laser pointers, additional pneumatically controlled switches may be present as well. For example, in one variation, a red laser pointer is mounted on the right side of the frame, and a green laser pointer is mounted on the left side of the frame. Two pneumatically controlled switches are provided, one on each side of the users head. Each switch would control a separate laser pointer. For example, the red laser pointer could be controlled by blowing to the right, and the green laser pointer could be controlled by blowing to the left. This type of control would permit both a red dot and a green dot to be on the target simultaneously. If desired, the red laser pointer and the green laser pointer could be placed on the same side of the frame, as long as the pneumatically controlled switches are located on opposite sides of the frame. Alternatively, a multicolor laser pointer could be mounted on the frame along with two pneumatically controlled switches. One switch would toggle the laser pointer on and off, and the other switch would control which color was being generated by the laser pointer.

Figure 4:
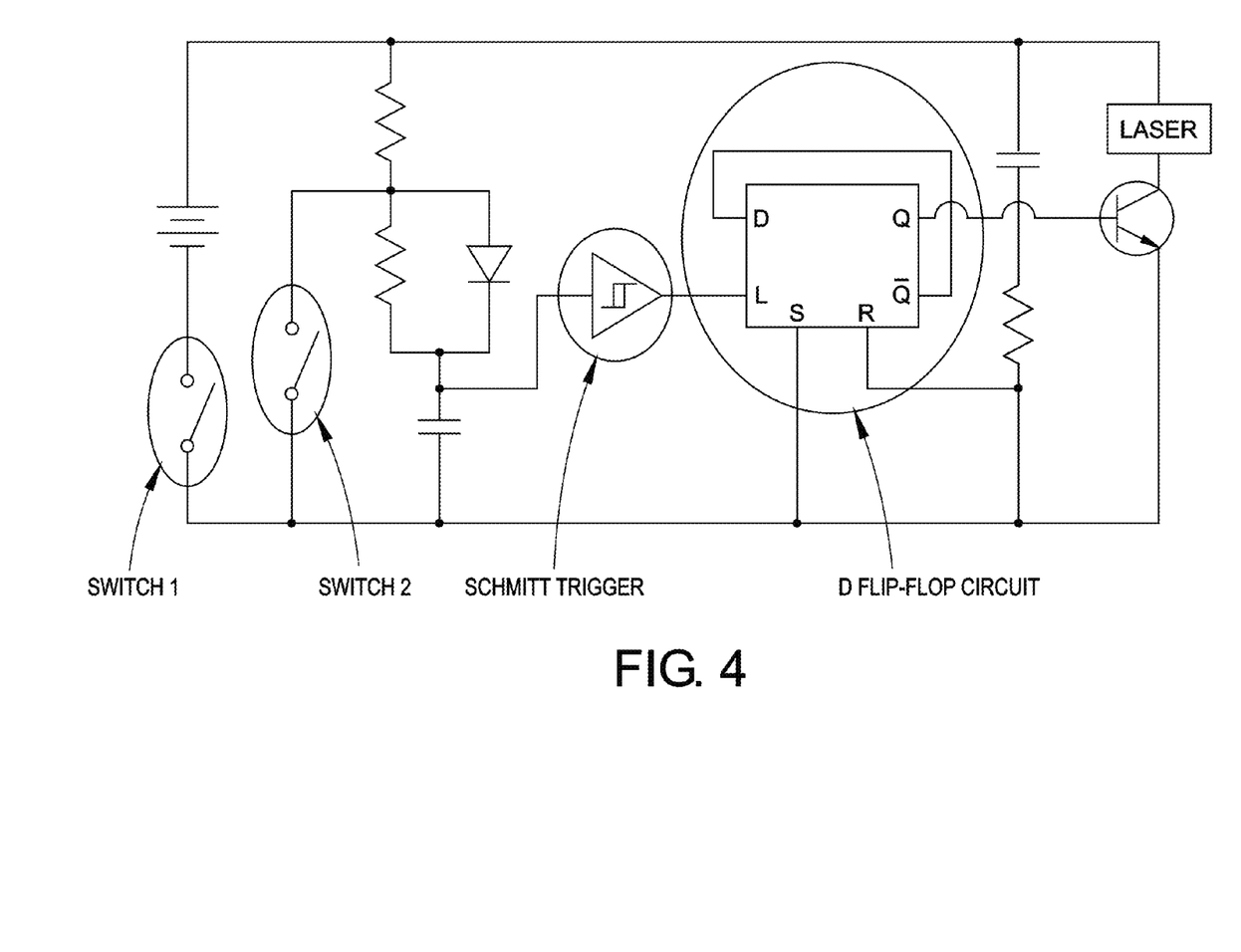
FIG. 4 is a circuit diagram or schematic illustrating the control of the laser pointer.

FIG. 4 is a circuit diagram showing the control of the laser pointer via the pneumatically controlled switch. Beginning at the left side, Switch 1 is an on/off switch that determines whether the laser pointer can be activated at all. This on/off switch may be located on the laser pointer or on the battery pack, and is usually electromechanical in nature. Switch 2 is the pneumatically controlled switch. The pneumatically controlled switch operates by sensing the difference in pressure between a high port and a low port, and operates based on the time period for which a differential pressure above a specified threshold level is applied. The threshold level can be adjusted by changing the leftmost capacitor in the diagram. A data or delay (D) flip-flop circuit is used to control the laser emission. When Switch 1 is closed, the laser pointer is in the ON state, or in other words is able to receive user input and be toggled on/off. Switch 2 provides the toggle function. Initially, blowing into the blow switch closes Switch 2 and turns the laser on to emit the laser beam. After the pressure is removed, Switch 2 is opened, and the laser beam is emitted until Switch 2 is closed again. Put another way, Switch 1 controls whether the laser pointer device is ON or OFF. Switch 2 changes the state of the laser beam (from ON to OFF, or from OFF to ON). An inverting Schmitt trigger is used to add hysteresis and prevent unwanted rapid switching of the laser emission/debounce the circuit. The input voltage to the circuit must fall below a threshold value before the laser pointer is toggled on/off. The circuit always turns on with the laser in the OFF state.

Figure 5:
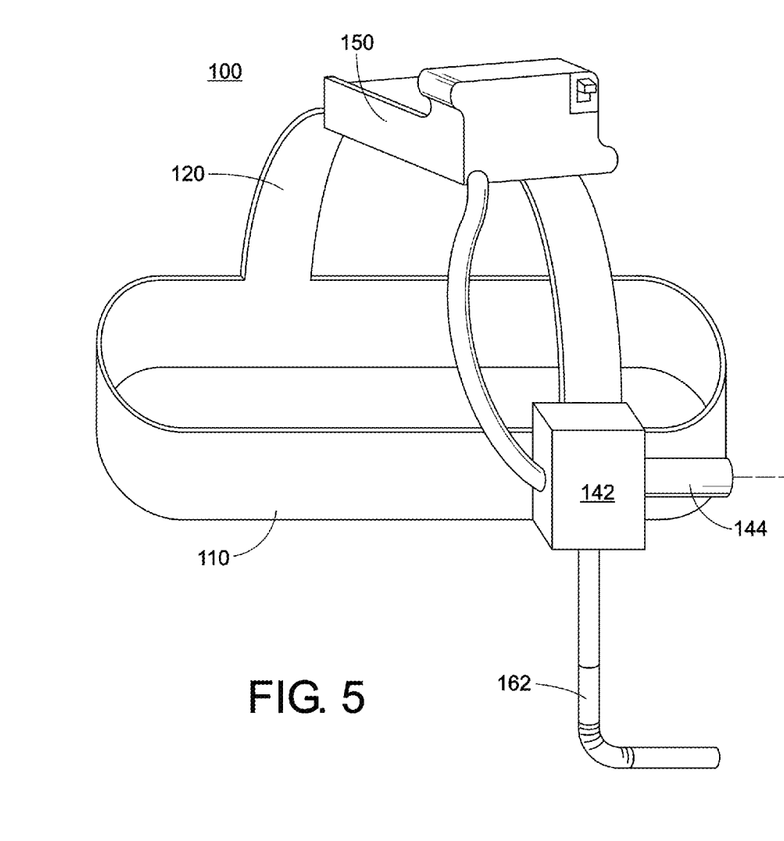
FIG. 5 is an illustration of another embodiment of the head-mounted pointing device of the present disclosure.

FIG. 5 is a perspective view of the head-mounted pointing device 100, showing the minimum components. The device includes the frame made of the circumferential headband 110 and the cross strap 120. The battery pack 150 is located here at the center of the cross strap. The base 142 of the laser pointer is mounted on the right side of the frame, with the muzzle 144 pointing forward. The flexible straw 162 extends from the base downwards.

Figure 6:
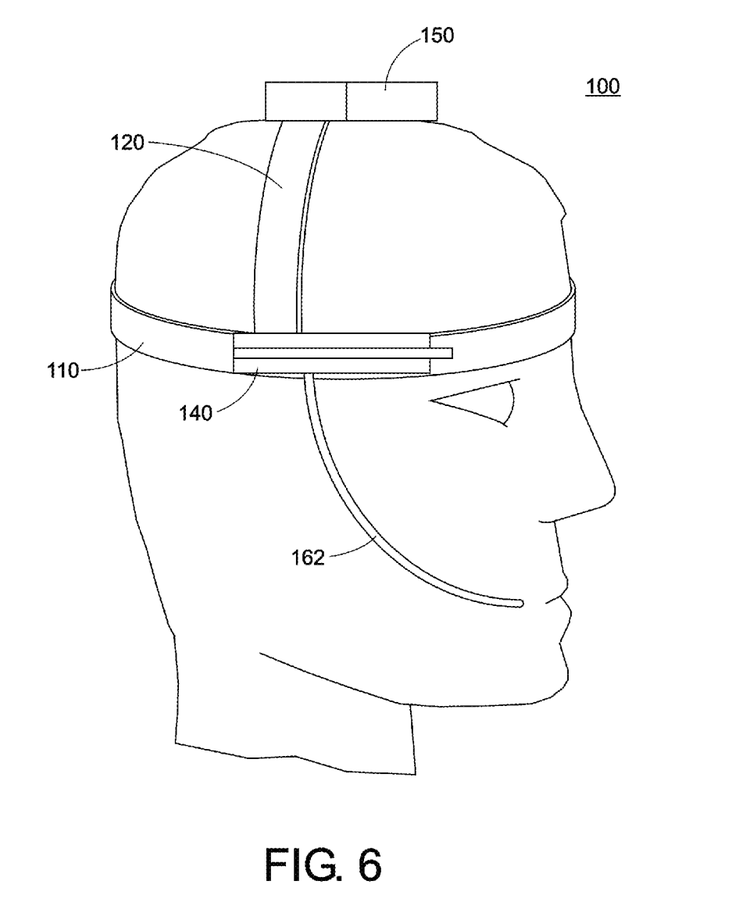
FIG. 6 depicts the head-mounted pointing device of FIG. 5 on the head of the user.

FIG. 6 depicts the head-mounted pointing device 100 and on the head of the user. The circumferential headband 110 and the cross strap 120 form the frame. The battery pack 150 is located upon the user's head. The laser pointer 140 is on the right side of the user's head. The straw 162 extends down to the user's mouth, and the user's breathing controls the laser pointer.

The resulting head-mounted pointing device provides the ability for a trainer surgeon to direct a resident through a given surgical procedure, facilitating teaching in the operating room. This device can be used for all laparoscopic surgical cases, open surgical cases, and may have many other potential medical and nonmedical applications for visual communication of information when it is not possible to use the hands or voice to communicate the information.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A head-mounted pointing device for use by a trainer in a surgical procedure, comprising:
    an adjustable circumferential headband;
    a cross strap extending between opposite sides of the circumferential headband;
    a laser pointer mounted on a right or left side of the circumferential headband wherein the laser pointer, when activated, provides a beam of light at a location dictated by the trainer;
    a battery pack for supplying power to the laser pointer when activated; and
    a first user-operated pneumatically controlled switch for activating the laser pointer, the first switch including a flexible straw connected to a pressure transducer, the first switch extending from the base of the laser pointer, and the first switch being configured to sense the difference in pressure between a high port and a low port, and switching between states when a differential pressure above a specified threshold level has been applied for a specified time period; and
    a mount on a front side of the circumferential headband, the mount having an arm and a grip;
    wherein by moving the trainer's head and engaging the first switch to activate the laser pointer, the trainer can point the beam of light at a designated target during the surgical procedure.

2. The pointing device of claim 1, wherein the battery pack is mounted at the center of the cross strap.

3. The pointing device of claim 1, wherein the battery pack is mounted on the side of the circumferential headband opposite the laser pointer.

4. The pointing device of claim 1, wherein the battery pack is mounted on the side of the circumferential headband behind the laser pointer.

5. The pointing device of claim 1, wherein the laser pointer emits a red or green colored beam.

6. The pointing device of claim 1, further comprising means for controlling the circumference of the headband.

7. The pointing device of claim 1, wherein the laser pointer includes a base and a muzzle.

8. The pointing device of claim 1, wherein the laser pointer is a multicolor laser pointer, and a second pneumatically controlled switch is present to control the color being generated by the laser pointer, the second pneumatically controlled switch being located on an opposite side of the frame from the first pneumatically controlled switch, and configured to operate in the same manner as the first pneumatically controlled switch.

9. A head-mounted pointing device, comprising:
a frame formed from a circumferential headband and a cross strap that extends between opposite sides of the circumferential headband;
a battery pack mounted at the center of the cross strap;
a first laser pointer mounted on a right side of the circumferential headband, the first laser pointer emitting a first color;
a first pneumatically controlled switch for controlling the laser pointer, the switch including a flexible straw extending from the base of the first laser pointer and is connected to a first pressure transducer, the first switch being configured to sense the difference in pressure between a high port and a low port, and switching between states when a differential pressure above a specified threshold level has been applied for a specified time period;
a second laser pointer mounted on a left side of the circumferential headband, the second laser pointer emitting a second color different from the color;
a second pneumatically controlled switch for controlling the second laser pointer, the second switch including a flexible straw that extends from the base of the second laser pointer and is connected to a second pressure transducer, the second switch being configured to sense the difference in pressure between a high port and a low port, and switching between states when a differential pressure above a specified threshold level has been applied for a specified time period;
means for changing the size of the circumferential headband;
means for changing the size of the cross strap; and
a mount on a front side of the circumferential headband, the mount having an arm and a grip.

10. A method of using a head-mounted pointing device to point to a given target during a surgical procedure, comprising:
donning the head-mounted pointing device;
toggling on a laser pointer of the pointing device by breathing at a pneumatically controlled switch to generate a differential pressure above a specified threshold level for a specified time period to activate a laser beam; and
pointing the laser beam at the given target;
wherein the head-mounted pointing device comprises:
a circumferential headband;
a cross strap extending between opposite sides of the circumferential headband;
a battery pack;
the laser pointer mounted on a right or left side of the circumferential headband; and
the pneumatically controlled switch extending from a base of the laser pointer.

11. The method of claim 10, further comprising toggling off the laser pointer of the pointing device by breathing at the pneumatically controlled switch to generate the differential pressure above the specified threshold level for the specified time period to deactivate the laser beam.

12. The method of claim 10, wherein the pneumatically controlled switch uses a binary control.

13. The method of claim 10, wherein the pneumatically controlled switch uses sip-and-puff control.

14. The pointing device of claim 1, wherein the first pneumatically controlled switch includes a circuit formed by two switches, an inverting Schmitt trigger, and a D flip-flop circuit.

* * * * *